United States Patent [19]

Kirsch et al.

[11] Patent Number: 5,678,995
[45] Date of Patent: Oct. 21, 1997

[54] ENOSSAL IMPLANT FOR TOOTH REPLACEMENT

[75] Inventors: Axel Kirsch, Stuttgart; Walter Dürr, Remchinen, both of Germany

[73] Assignees: IMZ Fertigungs- und Vertriebs gesellschaft fuer dentale Technolgie mbH, Filderstadt; Eberle Medizintechnische Elemente GmbH, Wurmberg, both of Germany

[21] Appl. No.: 531,279

[22] Filed: Sep. 20, 1995

[30] Foreign Application Priority Data

Sep. 21, 1994 [DE] Germany .................. 44 33 671.3

[51] Int. Cl.⁶ .................. A61C 13/28; A61C 13/12
[52] U.S. Cl. .................. 433/169; 433/172
[58] Field of Search .................. 433/169, 172, 433/173, 174, 175, 176

[56] References Cited

U.S. PATENT DOCUMENTS

| | | | |
|---|---|---|---|
| 4,957,437 | 9/1990 | Shimura et al. | 433/169 |
| 5,026,280 | 6/1991 | Dürr et al. | 433/175 |
| 5,040,982 | 8/1991 | Stefan-Dogar | 433/169 |
| 5,362,234 | 11/1994 | Salazar et al. | 433/169 |

FOREIGN PATENT DOCUMENTS 2007141  2/1994  Russian Federation ............. 433/174

Primary Examiner—Cary E. O'Connor
Attorney, Agent, or Firm—Hill, Steadman & Simpson

[57] ABSTRACT

An enossal implant includes a base member, a one-piece spacer member and fastening head which has a skeleton structure composed of metal and plastic material. The spacer sleeve has a blind bore with threads in the fastening head portion for receiving a threaded implant post. The skeleton structure has cavities in a metal body filled with an elastic plastic material to enable the spacer sleeve to be compressed in an axial direction and also to bend in response to bending stresses.

17 Claims, 5 Drawing Sheets

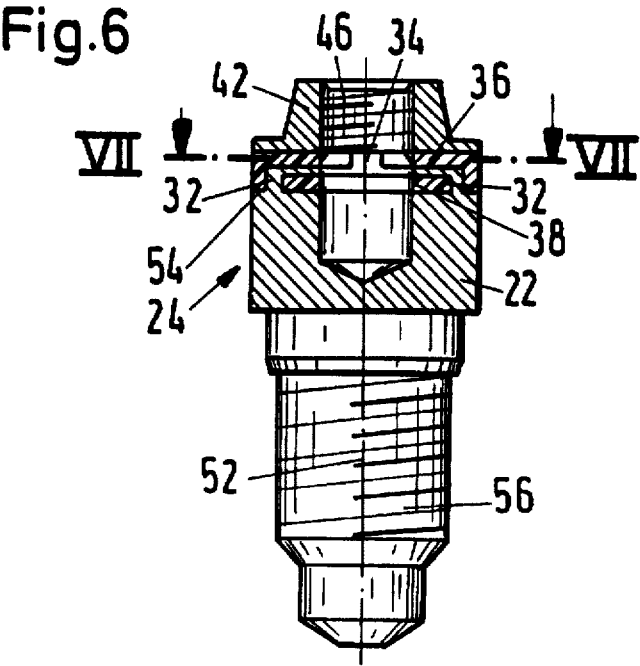
Fig.6
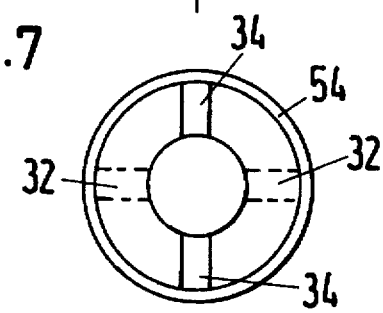
Fig.7
Fig.8
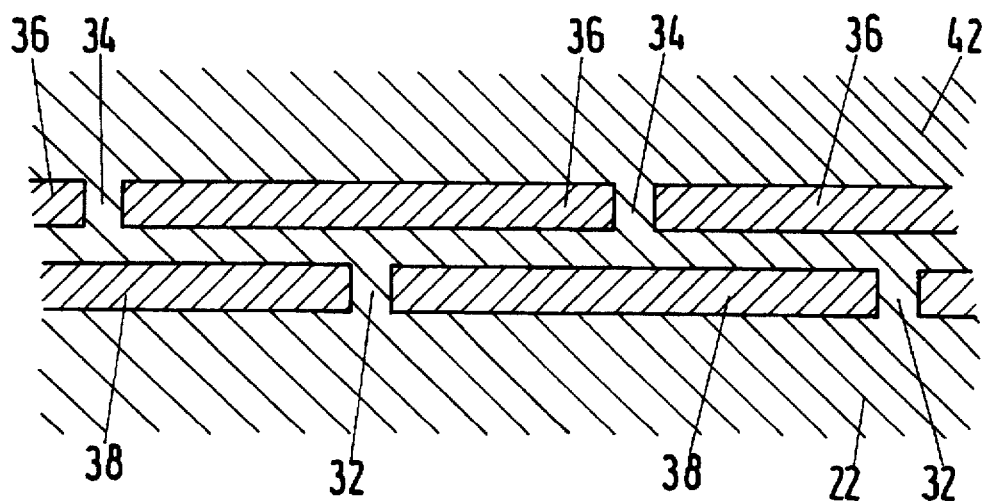

5,678,995

1

ENOSSAL IMPLANT FOR TOOTH REPLACEMENT

BACKGROUND OF THE INVENTION

The present invention is directed to an enossal implant for a firmly-seated tooth replacement or dental prosthesis. The implant has an implantable, cylindrical base member of metal with an end face with a blind bore provided with internal threads, a spacer sleeve of metal that is open toward the tooth replacement and can be screwed into the blind bore of the base member. The spacer sleeve has an internal bore with a threaded portion open toward the tooth replacement and is closed at an end facing away from the tooth replacement. The spacer sleeve has a cylindrical extension region with the same outside diameter as the base member and forms an annular shoulder pressing against an end face of the base member. The cylindrical extension region terminating in a fastening head having a seating surface for the tooth replacement and a fastening screw or implant post for holding the tooth replacement on the seating surface is threaded into the threaded portion of the internal bore of the spacer sleeve.

U.S. Pat. No. 5,026,280, whose disclosure is incorporated herein by reference thereto and which claims priority from German Patent Applications 38 39 724 and 39 09 580, discloses an enossal implant for a firmly-seated tooth replacement, which includes a base member and a spacer member. In this arrangement, an implant post is concentrically surrounded in the regions by an intermediate element composed of elastic plastic material. The elastic intermediate element comprises an inside bore whose diameter is greater facing toward the dental prosthesis and is larger than the outside diameter of the implant post. The implant post of this device, likewise, freely penetrates to the inside bore of the elastic intermediate element in a region adjacent to the dental prosthesis without pressing against the inside walls of the inside bore of the intermediate element and a moving rod effect thus occurs together with a vertically resilient support of the dental prosthesis relative to the implant post, which assures a limited elastic mobility of the dental prosthesis relative to the base member. An elastic intermediate element arranged concentrically relative to the implant post also effects a damped, elastic bearing, whereby the dampening occurs in an axial direction via the volume elasticity of the intermediate element, so that the dampening is achieved in a lateral direction due to the implant post acting according to the moving rod principle in conjunction with the material of the intermediate element. As a result thereof, the compressive and tensile forces that arise when swivelling the dental prosthesis seated by the implant post, as well as bending moments that act on the intermediate element, can be introduced into the base member and, thus, into the jawbone without the risk of fatigue fractures.

The implant of this device has definitely proven itself in practice. However, it would be desirable to improve, in particular, the axial-elastic bearing of the dental prosthesis even more.

SUMMARY OF THE INVENTION

The present invention is based on the object of developing an enossal implant of the above type, which has reduced manufacturing costs. A reliable elastic dampening bearing of the dental prosthesis is provided both in an axial as well as a transverse or, respectively, shearing stress direction.

This object is inventively achieved in an enossal implant for a firmly-seated tooth replacement having an implantable, cylindrical base member of metal with an end face with a blind bore provided with internal threads, a spacer sleeve of metal which is threaded into the blind bore and has an internal bore with a threaded portion open toward the tooth replacement and is closed at an end facing away from the tooth replacement, said spacer sleeve having a cylindrical extension region with the same outside diameter as the base member and forming an annular shoulder pressing against the end face of the base member, a fastening head with a seating surface for a tooth replacement, and a fastening screw or implant post for holding the tooth replacement on the seating surface as the screw is threaded into the threaded portion of the internal bore of the spacer sleeve. The improvements are that the fastening head is part of the spacer sleeve and the spacer sleeve has a skeleton structure of metal and elastic plastic material connecting the cylindrical extension to the fastening head. Preferably, the skeleton structure is formed by at least one planar cavity extending transverse to a longitudinal axis of the spacer sleeve and an elastic plastic material fills up said cavity. In addition, the threaded portion is provided only in the area of the fastening head so that the skeleton structure is compressible in the direction of the longitudinal axis of the spacer sleeve and capable of excursion perpendicular to the longitudinal axis given bending stresses being integrally applied thereto. Preferably, two or more cavities are provided, and each of the walls of each cavity are connected to each other adjacent one area with the connection of one cavity being offset from the connection of the adjacent cavities.

It has been thereby provided that the skeleton structure in the cylindrical portion comprises at least one circular disk-shaped cavity which is filled with the elastic plastic or the like, whereby the circular disk-shaped sectors of the skeleton structure adjacent in axial direction are connected to one another via at least one circumference-proximate axial edge web.

The invention also proposes that the axial edge webs allocated to the cavities are arranged offset from one another in a circumferential direction.

It is also inventively proposed that the adjacent circular disk-shaped sectors of the skeleton structure are connected to one another via, respectively, two circumference-proximate axial edge webs that are arranged diametrically opposite one another with respect to the circumference.

It is also provided that the pair of axial edge webs respectively allocated to one of the cavities are respectively arranged angularly offset relative to the other webs of the adjacent cavity that follows one another in the axial direction.

The invention also provides that the pair of axial edge webs respectively allocated to one of the cavities are respectively arranged offset by 180° relative to one another in the cavities that follow one another in the axial direction. The invention also proposes that the plastic component of the intermediate element is fashioned coherently in and of itself.

It is also inventively proposed that the region of the skeleton structure comprises a smaller outside diameter than the cylindrical extension region and of the base member and that the skeleton structure is surrounded by a plastic cladding forming a constituent part of the plastic component of the elastic filling material, the outside diameter of said plastic cladding coinciding with that of the base member and of the cylindrical extension region adjacent to the skeleton structure.

It is also provided that the circumferential wall of the blind bore of the spacer sleeve has its receptacle region that is not provided with an inside thread and that faces toward the base member lined with a plastic cladding material that forms a constituent part of the plastic component of the intermediate element and the inside diameter of said plastic cladding corresponding to the outside diameter of the implant post in a peg region of the implant post that is not provided with outside threads and faces away from the dental prosthesis or replacement tooth.

It is also provided that the plastic cladding also completely lines the floor of the receptacle region of the blind bore.

The invention further provides that the plastic components of the skeleton structure are anchored form-fitted in the extension region and/or the fastening head with respect to the axial direction.

Finally, the invention provides that the plastic cladding comprises an annular lip that engages into an all-around circumferential annular channel formed in the extension region and/or in the fastening head.

As in the implant of the above-mentioned U.S. Patent, the polyoxymethylene, for example, can be employed in the invention as the plastic material for the plastic component of the elastic intermediate element. The plastic components are preferably integrally, coherently manufactured in an injection molding process.

The invention is based on the surprising perception that one succeeds in achieving a clearly improved elastically dampened support of the dental prosthesis, both in view of compressive stresses as well as shearing stresses in that the dental prosthesis is rigidly attached only to the fastening head with the implant post and the fastening head itself is in communication via a rubber-bonded-to-metal-like metal-plastic structure with that part of the spacer sleeve rigidly screwed into the base member so that all metal components of the spacer sleeve are manufactured of one piece of titanium or, respectively, a titanium alloy.

When, as provided in a specific embodiment of the invention, the plastic component of the intermediate element is anchored form-fitted in the extension region of the base member and/or in the fastening head, preferably in both of the aforementioned component parts, such that forces acting in the axial direction can be absorbed, an especially desirable strength of the intermediate elements with respect to axial stresses occur that can be beneficial in a number of applications, also due to the stiffening effect that is achieved.

Other advantages and features of the invention will be readily apparent from the following description of the preferred embodiments, the drawings and claims.

BRIEF DESCRIPTION OF THE DRAWINGS

FIG. 6 is a cross sectional view with portions in elevation of a modification of the first embodiment of the spacer sleeve of the implant of the present invention;

FIG. 7 is a cross sectional view taken along the lines VII—VII of FIG. 6; and

FIG. 8 is a developed view of an outer surface of the embodiments of FIGS. 5 and 6.

DESCRIPTION OF THE PREFERRED EMBODIMENTS

Figure 1:
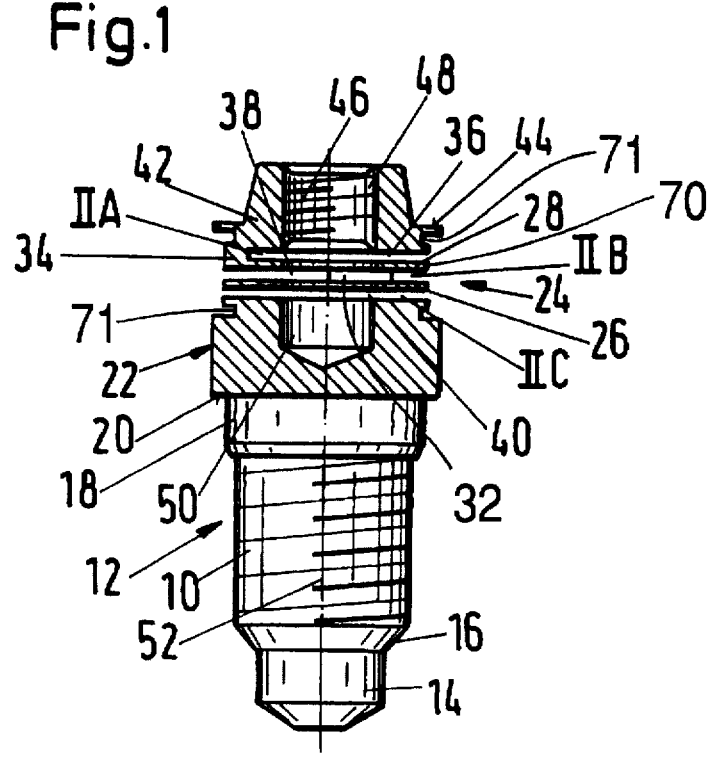
FIG. 1 is a cross sectional view with portions in elevation of a spacer sleeve in accordance with the present invention without the plastic components and having three transverse planar cavities which lie in planes IIa, IIb and IIc.
Figure 3:
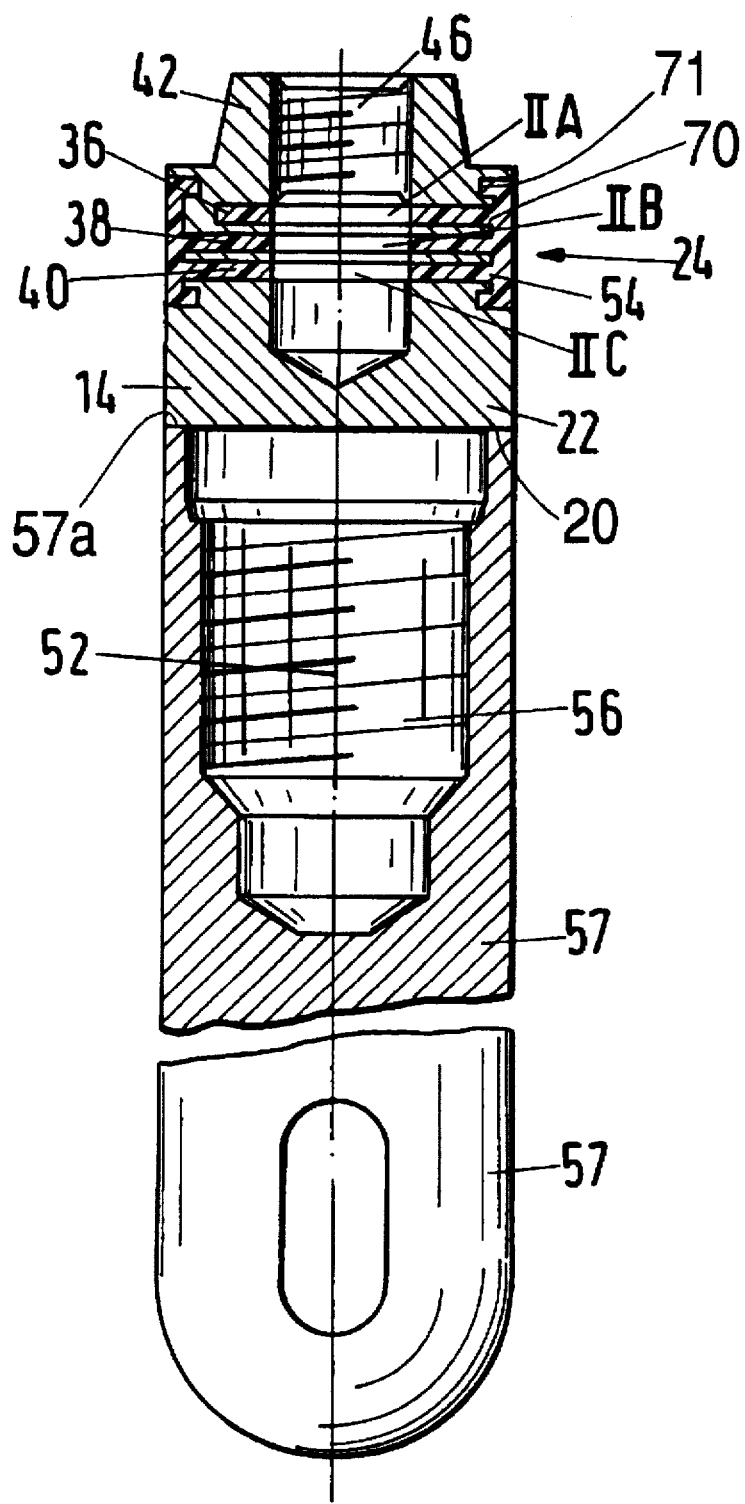
FIG. 3 is a cross sectional view with portions in elevation of the spacer sleeve of FIG. 1 having a plastic component being mounted in a base member of the device.

The principles of the present invention are particularly useful in an enossal implant having a base member 57 and a spacer sleeve 12, which are both formed of titanium and are illustrated in FIG. 3. As best illustrated in FIG. 1, the cylindrical spacer sleeve 12 is provided with outside threads in a threaded region 10, which will be threaded in a blind bore 56 of the base member 57, as shown in FIG. 3. Below the threaded region 10, the spacer sleeve 12 has a peg region 14 at its end which is placed at the bottom. This is not provided with outside threads and it merges into the threaded region 10 by a conical bevel 16.

The spacer sleeve 12 above the threaded region 10 has a cylindrical fit region 18, which is free of any threads. This fit region 18 has an enlarged outside diameter compared to the threaded region 10 and merges via an annular shoulder 20 into an extension region 22 of an enlarged diameter that has a smooth cylindrical circumferential surface. As illustrated in FIG. 3, the shoulder 20 rests on an end face 57a of the base member 57 and the region 22 has an outer diameter the same as the outer diameter of the base member 57.

Figure 2A:
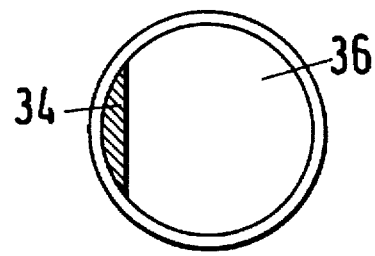
FIGS. 2a, 2b and 2c are cross sectional views taken on the planes IIa, IIb and IIc, respectively.
Figure 2B:
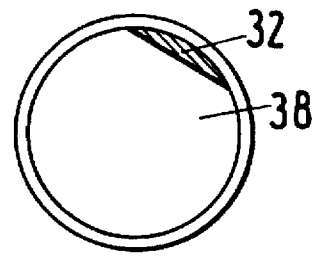
Figure 2C:
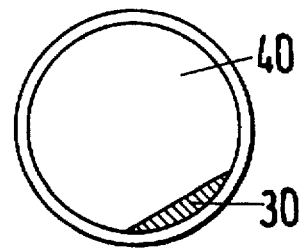

An upper portion of the region 22 is provided with a skeleton structure 24 having two disk-shaped sectors 26 and 28 which coact to form circular planar disk-shaped cavities 36, 38 and 40. The two disk-shaped sectors 26 and 28 are connected by axial edge webs 30, 32 and 34, of which only the webs 34 and 32 are visible in FIG. 1 and the web 30 is shown in FIG. 2c. As illustrated in FIGS. 2a, 2b and 2c, the webs 30, 32 and 34 are displaced approximately 120° relative to each other so that there is an offset between the web 34, which connects the member 28 to a fastening head portion 42, and the web 32, which interconnects the sectors 26 and 28 together, and, finally, an offset between the web 30, which connects the sector 26 to the lower portion of the region 22.

The skeleton structure 24 has a smaller diameter than the cylindrical extension region 22 to form a circumferential groove 70. The groove 70 has deeper cuts or grooves 71 at each end.

The fastening head 42 provides a firm seat for the dental prosthesis, which is not shown in FIG. 1. The fastening head 42 is provided with a conical fit surface, whereas the conical circumferential surface of the fastening head is provided with a seating shoulder 44 for receiving a pressing surface of the prosthesis.

The spacer sleeve 12 is provided with a blind bore 46, which extends through the fastening head 42, the skeleton structure 24 and into the extension region 22. The blind bore 46 has an inside or internal thread 48 in the region of the fastening head 42, whereas the rest of the bore in a receptacle region 50 lying farther toward the bottom has no threads, just like in the region of the sectors 26 and 28.

As a result of the arrangement of the axial edge webs 30, 32 and 34, which are circumferentially offset relative to one another, the intermediate skeleton structure 24, as a result of the correspondingly easily reversible bends of the edge webs 30, 32 and 34, is axially compressible in the direction of a longitudinal or middle axis 52 of the spacer sleeve 12. The structure 24 is also tiltable to a limited extent relative to the longitudinal axis 52, as a result whereof the fastening head 42 is movable to a limited extent relative to the extension region 22 of the spacer sleeve 12.

To complete the spacer sleeve 12, the cavities 36, 38 and 40, as illustrated in FIG. 3, are filled with an elastic plastic material, such as polyoxymethylene. The plastic component formed by the plastic material filling the cavities 36, 38 and 40 also comprises a plastic cladding 54 that fills the groove 70 and cuts 71 to completely surrounds the spacer sleeve 12 in the region of the skeleton structure 24 so that the spacer sleeve 12 has the same outside diameter as the region of the extension region 22.

As also illustrated in FIG. 3, the spacer sleeve 12 is inserted in the base member 57 with the shoulder 22 engaging an end face 57a.

Figure 4:
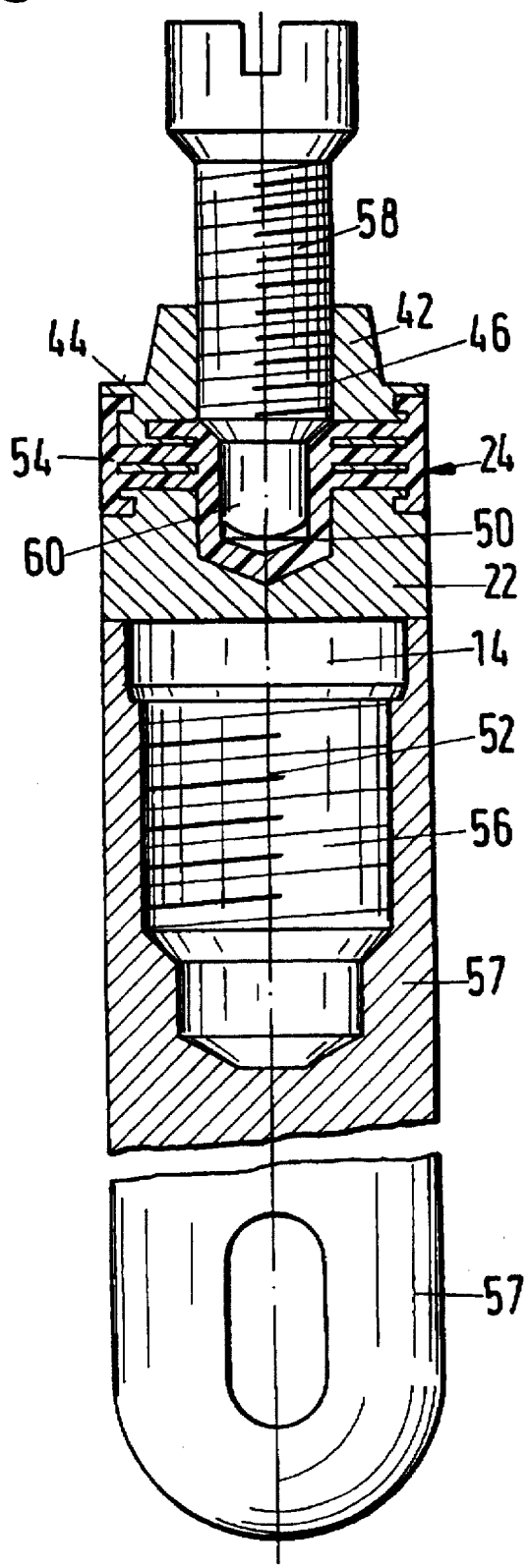
FIG. 4 is a cross sectional view of a modification of the enossal implant of the present invention with portions in elevation for purposes of illustration.
Figure 5:
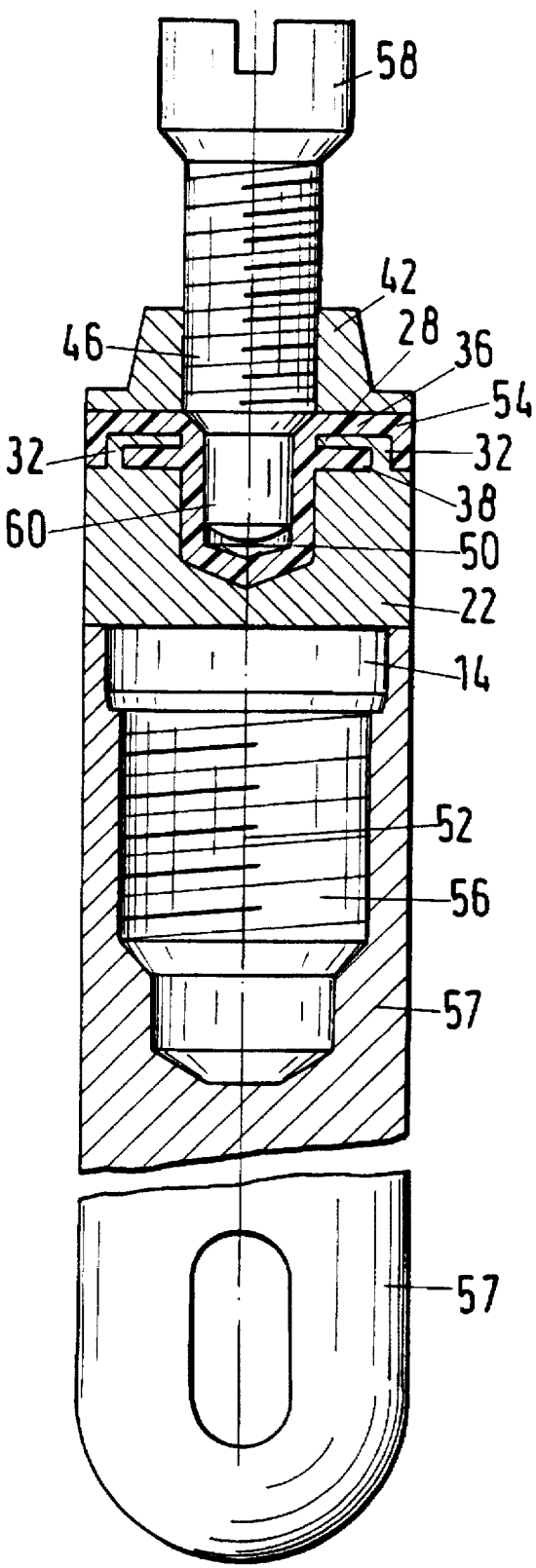
FIG. 5 is a cross sectional view with portions in elevation of a first embodiment of the enossal implant of the present invention.

A modification is illustrated in FIG. 4. In this modification, the implant post 58, which is constructed as a fastening screw, is threaded into the blind bore 46 of the spacer sleeve 12. A correspondingly fashioned annular seating surface of the dental prosthesis (not shown) is then capable of being pressed against the seating shoulder 44 of the fastening head 42. A peg region 60 of the implant post 58 is not provided with outside threads and enters into the receptacle region 50 of the blind bore 46 of the spacer sleeve 12. This receptacle region 50 in the exemplary modification of FIG. 4, by contrast to that of FIGS. 1 and 3, is completely lined with a plastic cladding that forms a coherent, one-piece plastic component together with the plastic cladding 54 and the plastic compound that fills the cavities 36, 38 and 40. This plastic component can be formed, preferably, by an injection molding process.

FIGS. 3 and 4 also show that the plastic cladding 54 of the plastic component of the intermediate element is anchored form-fitted both in the extension region 22 of the base member as well as the fastening head 42 by having annular lips of the plastic component engaged in an annular channel or groove 71 of FIG. 1, which is at the end of the annular groove 70. A form-fitted anchoring of the plastic component of the intermediate element is, thus, assured in the axial direction, both in the extension region 22 of the base member as well as in the fastening head 42. As a result thereof, forces acting in an axial direction can be positively absorbed.

FIGS. 5-8 show a first embodiment of the invention with a modification thereof. In this embodiment, two edge webs 34 are allocated to the cavity 36 and two edge webs 32 are allocated to the cavity 38. Each of the two edge webs 34 lie diametrically opposite one another, as do the two edge webs 32, and, as illustrated in FIG. 7, the webs 34 are offset 90° from the pair of webs 32. An especially beneficial dampening-elastic setting of the intermediate element can be achieved as a result of this spatial arrangement of the pair of edge webs 32 and 34 and the corresponding, plastic-filled cavities, which correspondingly are illustrated in the developed view shown in Fig. 8. The dampening-elastic properties can be modified further according to the purpose by a different construction of the width of the edge webs and/or a different angular arrangement of the edge webs both in the individual cavities as well as in the successive cavities in the relative arrangement.

In that the dental prosthesis, which is not shown in the illustrated embodiments of the invention, is firmly attached only to the fastening head 42 that has limited elastic mobility relative to the extension region 22 of the spacer sleeve 12 with the fastening screw or implant post 58, the dental prosthesis is elastically seated overall relative to the base member 57 both in the sense of an axial compression as well as in the direction of shearing stresses of the dental prosthesis. In the exemplary embodiment of FIG. 5, like that of the modification of FIG. 4, the plastic cladding 50 additionally contributes to the elastic bearing of the dental prosthesis. This plastic cladding 50 dampens lateral excursions of the peg region 60 of the implant post 58 with respect to the longitudinal middle axis 52.

Both individual as well as arbitrary combinations of the features of the invention disclosed in the above specification, in the drawings, as well as in the claims can be critical for realizing the various embodiments of the invention.

Although various minor modifications may be suggested by those versed in the art, it should be understood that we wish to embody within the scope of the patent granted hereon all such modifications as reasonably and properly come within the scope of our contribution to the art.

We claim:

1. In an enossal implant for a firmly-seated tooth replacement having an implantable, cylindrical base member of metal with an end face having a blind bore provided with internal threads, a spacer sleeve of metal that has an internal bore with a threaded portion open toward the tooth replacement and being closed at an end face away from the tooth replacement, said spacer sleeve having a cylindrical extension region with the same outside diameter as the base member and forming an annular shoulder pressing against the end face of the base member, a fastening head with a seating surface for the tooth replacement, and a fastening screw for holding a tooth replacement on the seating surface as the screw is threaded into the threaded portion of the internal bore of the spacer sleeve, the improvements comprising the fastening head being a portion of the spacer sleeve and at least one planar cavity extending transverse to a longitudinal axis of the spacer sleeve to form a skeleton structure between the cylindrical extension region and the fastening head, an elastic plastic material filling up said cavity, said threaded portion being provided only in said fastening head so that the spacer sleeve is a combined metal plastic member capable of being compressed in the direction of the longitudinal axis of the spacer sleeve and capable of excursion perpendicular to the longitudinal axis given bending stresses applied to said fastening screw.

2. In an enossal implant according to claim 1, wherein opposite walls of the planar cavity are interconnected via at least one circumferential approximate axial edge web.

3. In an enossal implant according to claim 2, wherein at least two cavities are spaced in the axial direction and separated from one another by a circular disk-shaped sector, the axial edge web allocated to one cavity being arranged offset from the other cavity in a circumferential direction.

4. In an enossal implant according to claim 3, wherein the circular disk-shaped sector of the skeleton structure is connected to adjacent structure of the spacer sleeve via two circumferentially approximately axial edge webs that are arranged diametrically opposite one another with respect to the circumference.

5. In an enossal implant according to claim 4, wherein a pair of axial edge webs allocated to one of the cavities is respectively arranged angularly offset relative to the pair of web edges for the other cavity axially adjacent thereto.

6. In an enossal implant according to claim 5, wherein the pair of axial edge webs allocated to the one cavity are respectively arranged offset by 90° relative to the pair of web edges of the adjacent cavity.

7. In an enossal implant according to claim 1, wherein the elastic plastic material filling up said cavity is constructed and fashioned coherently in a one-piece member.

8. In an enossal implant according to claim 1, wherein the skeleton structure comprises a smaller outside diameter than the base member and that the skeleton structure is surrounded by a plastic cladding forming a constituent part of the elastic plastic filling material for the cavities, the outside diameter of said plastic cladding coinciding with that of the base member and of a seating shoulder of the spacer sleeve.

9. In an enossal implant according to claim 1, wherein a circumferential wall of the internal bore of the spacer sleeve has a receptacle region that is free of inside threads and faces toward the base member lined with a plastic cladding that forms a constituent part of the elastic plastic filling material of the spacer sleeve, the inside diameter of said plastic cladding corresponding to the outside diameter of an implant post in a peg region of the implant post that is free of external threads and faces away from the tooth replacement.

10. In an enossal implant according to claim 9, wherein the plastic cladding also completely lines the floor of the receptacle region of the internal bore.

11. In an enossal implant according to claim 1, wherein the elastic plastic filling forms a plastic component for the skeleton structure anchored at the extension region and adjacent the fastening head with respect to the axial direction.

12. In an enossal implant according to claim 11, wherein the spacer sleeve in the region of the skeleton structure has a metal body with a reduced diameter filled with said elastic plastic filling material to form a plastic cladding, said plastic cladding being anchored form-fitted adjacent the extension region and the fastening head.

13. In an enossal implant according to claim 12, wherein the plastic cladding comprises an annular lip that is engaged into an all-around circumferential annular channels adjacent the extension region and the fastening head.

14. In an enossal implant according to claim 1, wherein the skeleton structure comprises three planar cavities extending transversely to the longitudinal axis, said three cavities being separated by a pair of sector pieces, the pair of sector pieces being interconnected by a single edge web and each of the sector pieces being connected to adjacent portions of the head and cylindrical extension by edge webs, with the edge webs being circumferentially offset by approximately 120° relative to one another.

15. In an enossal implant according to claim 14, wherein the metal body of the skeleton structure has an annular circumferential groove receiving the elastic plastic filling material to form a cladding layer having an outer diameter the same as the outer diameter of the cylindrical extension region.

16. In an enossal implant according to claim 15, wherein the cladding has annular inwardly extending lips adjacent each edge thereof for anchoring the cladding in said spacer sleeve.

17. In an enossal implant for a firmly-seated tooth replacement having an implantable, cylindrical base member of metal with an end face having a blind bore provided with internal threads, a spacer sleeve of metal that has an internal bore with a threaded portion open toward the tooth replacement and being closed at an end face away from the tooth replacement, said spacer sleeve having a cylindrical extension region with the same outside diameter as the base member and forming an annular shoulder pressing against the end face of the base member, a fastening head with a seating surface for the tooth replacement, and a fastening screw for holding a tooth replacement on the seating surface as the screw is threaded into the threaded portion of the internal bore of the spacer sleeve, the improvements comprising the fastening head being a portion of the spacer sleeve, said spacer sleeve having a skeleton structure of metal and elastic plastic material between the cylindrical extension region and the fastening head, said threaded portion being provided only in said fastening head so that the spacer sleeve is a combined metal plastic member capable of being compressed in the direction of the longitudinal axis of the spacer sleeve and capable of excursion perpendicular to the longitudinal axis given bending stresses applied to said fastening screw.

* * * * *